(12) United States Patent
Chang et al.

(10) Patent No.: US 9,714,904 B2
(45) Date of Patent: Jul. 25, 2017

(54) SPHERICAL LIGHT-EMITTING STRUCTURE FOR INSPECTING WORKPIECE

(71) Applicants: Fu Tai Hua Industry (Shenzhen) Co., Ltd., Shenzhen (CN); HON HAI PRECISION INDUSTRY CO., LTD., New Taipei (TW)

(72) Inventors: Chih-Kuang Chang, New Taipei (TW); Li Jiang, Shenzhen (CN); Dong-Hai Li, Shenzhen (CN); Jian-Hua Liu, Shenzhen (CN); Dong-Sheng Liu, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 227 days.

(21) Appl. No.: 14/732,952

(22) Filed: Jun. 8, 2015

(65) Prior Publication Data

US 2016/0109378 A1     Apr. 21, 2016

(30) Foreign Application Priority Data

Oct. 15, 2014   (CN) .......................... 2014 1 0544891

(51) Int. Cl.
*G01N 21/88*     (2006.01)

(52) U.S. Cl.
CPC . *G01N 21/8806* (2013.01); *G01N 2021/8845* (2013.01); *G01N 2201/0627* (2013.01)

(58) Field of Classification Search
CPC ....... G01N 21/8806; G01N 2021/8845; G01N 2201/0627
See application file for complete search history.

(56) References Cited

U.S. PATENT DOCUMENTS

| 5,201,576 A  * | 4/1993 | Squyres ............. G01N 21/8806 356/394 |
| 2004/0190309 A1 * | 9/2004 | Bixler .................... A47G 33/08 362/565 |
| 2005/0231975 A1 * | 10/2005 | Bixler .................... A47G 33/08 362/565 |
| 2010/0085749 A1 * | 4/2010 | Bezgachev ........ G01N 21/9505 362/235 |
| 2011/0286200 A1 * | 11/2011 | Iimura .................... F21V 7/041 362/84 |
| 2012/0182711 A1 * | 7/2012 | Kolodin .................... F21V 5/04 362/84 |
| 2013/0021794 A1 * | 1/2013 | Chinniah ................... F21V 7/04 362/235 |
| 2013/0070464 A1 * | 3/2013 | Shinohara ................. F21V 3/00 362/373 |

* cited by examiner

*Primary Examiner* — Mary Ellen Bowman
(74) *Attorney, Agent, or Firm* — Steven Reiss

(57) ABSTRACT

A light-emitting structure includes two outer shells configured to be joined together to cooperatively define a receiving space therein, a connecting assembly configured to join the two outer shells together, and two light-emitting assemblies coupled to the connecting assembly and configured to emit light inside the receiving space. The two outer shells define a number of viewing holes therein for viewing inside the receiving space. The light-emitting assemblies shine light from a number of different angles inside the receiving space.

17 Claims, 3 Drawing Sheets

SPHERICAL LIGHT-EMITTING STRUCTURE FOR INSPECTING WORKPIECE

FIELD

The present disclosure relates to light-emitting structures, and more particularly to a spherical light-emitting structure for inspecting a plurality of surfaces of a workpiece.

BACKGROUND

The surfaces of a workpiece can be inspected by a charge-coupled device that captures a plurality of images of the surfaces of the workpiece. Each surface of the workpiece may need to be captured to be inspected.

BRIEF DESCRIPTION OF THE DRAWINGS

Implementations of the present technology will now be described, by way of example only, with reference to the attached figures.

DETAILED DESCRIPTION

Figure 1:
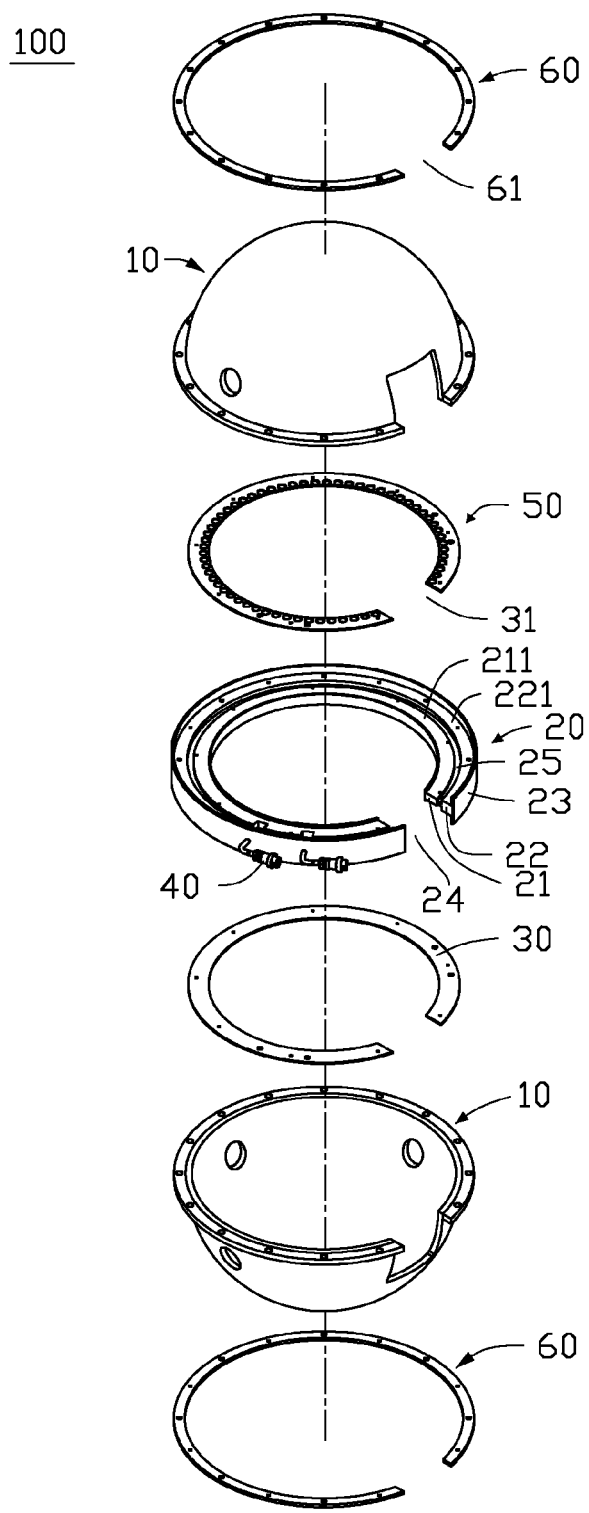
FIG. 1 is an exploded isometric view of an exemplary embodiment of a light-emitting structure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other word that "substantially" modifies, such that the component need not be exact. For example, "substantially cylindrical" means that the object resembles a cylinder, but can have one or more deviations from a true cylinder. The term "comprising" means "including, but not necessarily limited to"; it specifically indicates open-ended inclusion or membership in a so-described combination, group, series and the like.

Figure 2:
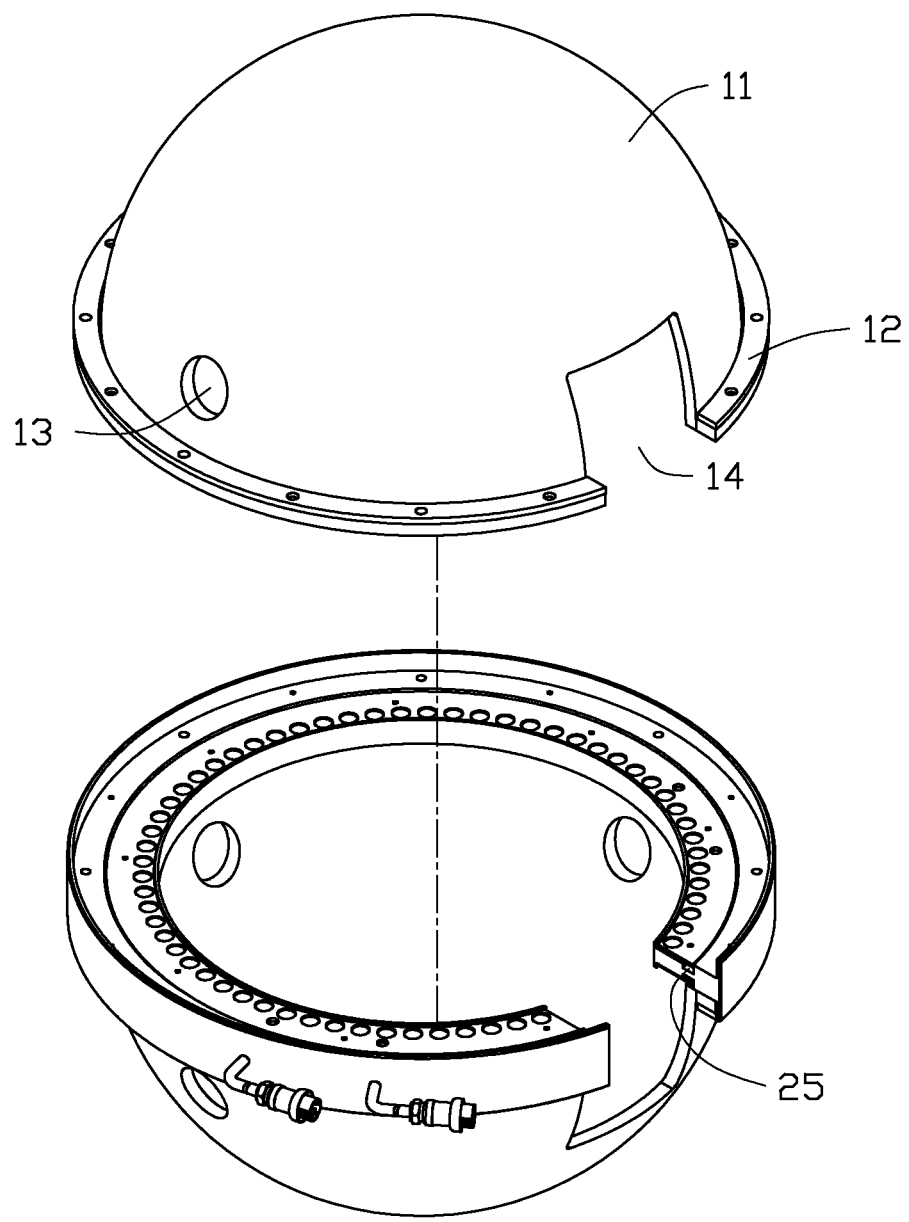
FIG. 2 is a partially assembled isometric view of the light-emitting structure.
Figure 3:
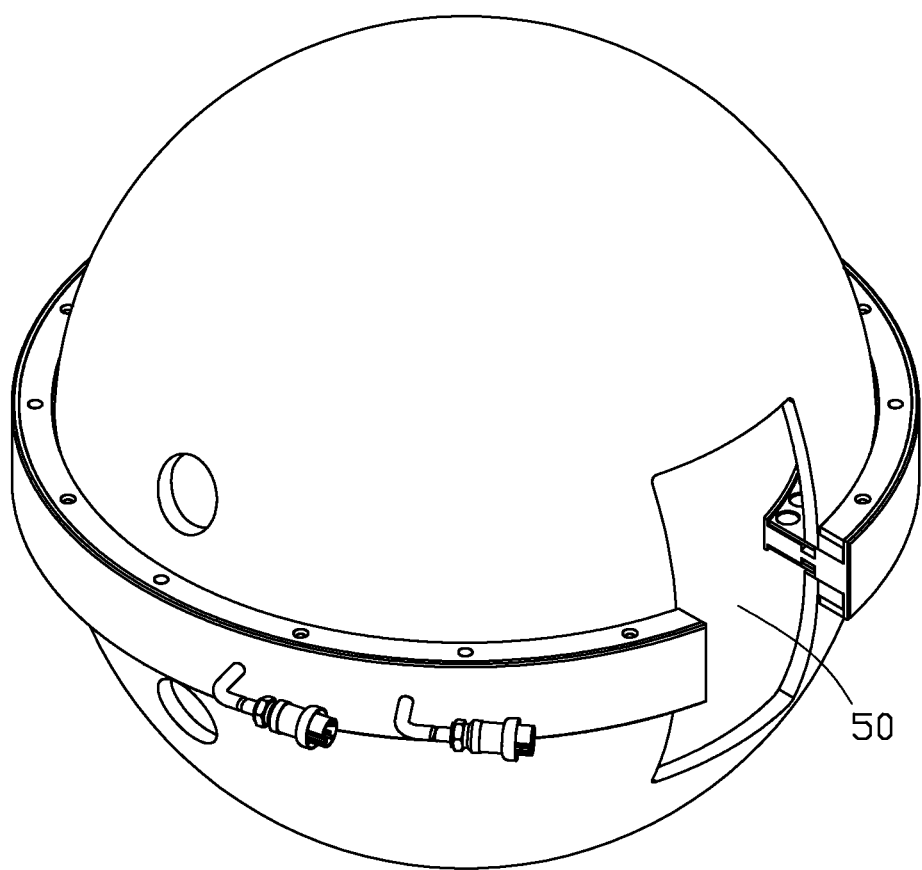
FIG. 3 is an assembled isometric view of the light-emitting structure.

FIGS. 1-3 illustrate an exemplary embodiment of a light-emitting structure 100. The light-emitting structure 100 can include two outer shells 10, a connecting assembly 20, and two light-emitting assemblies 30. In at least one embodiment, the light-emitting structure 100 is substantially spherical, and each outer shell 10 is substantially hemispherical. The connecting assembly 20 can connect the two outer shells 10 together. In at least one embodiment, the two outer shells 10 are substantially identical to each other, and the two light-emitting assemblies 30 are substantially identical to each other. The two outer shells 10 can cooperatively define a receiving space (not labeled) when joined together. The light-emitting structure 100 can be used for shining light onto a plurality of surfaces of a workpiece (not shown) for inspecting the workpiece. The workpiece can be received inside the receiving space.

Each outer shell 10 can include a dome-shaped main body 11, and a flange rim 12 protruding continuously around a peripheral edge of the main body 11. A plurality of viewing holes 13 can be defined in the main body 11 for viewing the workpiece received inside the receiving space. A first cutout 14 can be defined in an edge portion of the main body and the flange rim 12. In at least one embodiment, each end of the flange rim is flush with a corresponding edge of the first cutout 14.

The connecting assembly 20 can include a first connecting piece 21, a second connecting piece 22, and a third connecting piece 23. The first connecting piece 21, the second connecting piece 22, and the third connecting piece 23 can be substantially circular. The radius of the first connecting piece 21 can be less than the radius of the second connecting piece 22, and the radius of the second connecting piece 22 can be less than the radius of the third connecting piece 23. The two light-emitting assemblies 30 can be secured to the connecting assembly 20 by the first connecting piece 21, and the two outer shells 10 can be secured to the connecting assembly 20 by the second connecting piece 22. A second cutout 24 can be defined in the first connecting piece 21, the second connecting piece 22, and the third connecting piece 23. The first connecting piece 21 can include a pair of opposite supporting surfaces 211, and the second connecting piece 22 can include a pair of opposite fixing surfaces 221. Each light-emitting assembly 30 can be secured to the corresponding supporting surface 211 of the first connecting piece 21. Each outer shell 10 can be secured to the corresponding fixing surface 221 of the second connecting piece 22.

A plurality of channels (not shown) can be defined through the first connecting piece 21, the second connecting piece 22, and the third connecting piece 23. A plurality of connectors 40 can be inserted into the plurality of channels correspondingly to electrically connect the light-emitting assemblies 30 to a control unit (not shown). The control unit can control the light-emitting assemblies 30 to emit light.

A groove 25 can be defined between the first connecting piece 21 and the second connecting piece 22 on each side of the connecting assembly 20. The grooves 25 can be defined along a length of the connecting assembly 20. The grooves 25 can be used to receive electrical lines of the light-emitting assemblies 30.

Each light-emitting assembly 30 can be substantially circular. A third cutout 31 corresponding to the first cutout 14 and the second cutout 24 can be defined in the light-emitting assembly 30. Each light-emitting assembly 30 can include a plurality of light-emitting devices (not labeled) thereon. In at least one embodiment, the light-emitting devices are LED lights of difference colors.

In assembly, the light-emitting assemblies 30 can be secured to the corresponding supporting surfaces 211 of the first connecting piece 21, and the outer shells 10 can be secured to the corresponding fixing surfaces 221 of the second connecting piece 22. The first connecting piece 21 can define a plurality of first fixing holes (not labeled) in each of the supporting surfaces 211, and the second connecting piece 22 can define a plurality of second fixing holes (not labeled) in each of the fixing surfaces 221. The light-emitting assemblies 30 can define a plurality of third fixing holes (not labeled) corresponding to the first fixing holes, and the flange rim 12 of the outer shells 10 can define a plurality of fourth fixing holes (not labeled) corresponding to the plurality of second fixing holes. A plurality of first fixing members (not shown) can be inserted through the first fixing holes and the corresponding third fixing holes to secure the light-emitting assemblies 30 to the first connecting piece 21. A plurality of second fixing members (not shown) can be inserted through the second fixing holes and the corresponding fourth fixing holes to secure the outer shells 10 to the second connecting piece 22. The first cutouts 14, the second cutout 24, and the third cutouts 31 can be aligned with each other to cooperatively define an entranceway 50. The workpiece can be placed inside the receiving chamber by being passed through the entranceway 50.

The light-emitting structure 100 can further include two outer securing members 60. Each outer securing member 60 can define a plurality of fifth fixing holes (not labeled) therein. Each outer securing member 60 can be secured onto the flange rim 12 of the corresponding outer shell 10 by the plurality of second fixing members being inserted through the plurality of fifth fixing holes. A fourth cutout 61 can be defined in each outer securing member 60. The fourth cutout 61 can be aligned with the first cutouts 14, the second cutout 24, and the third cutouts 31.

In another embodiment, the light-emitting assemblies 30 and the outer shells 10 can be secured to the connecting assembly 20 by an adhesive, and the outer securing members 60 can be secured to the outer shells 10 by an adhesive.

In use, the plurality of light-emitting devices of the light-emitting assemblies 30 can shine light from a plurality of different angles onto the plurality of surfaces of the workpiece. Images of the plurality of surfaces of the workpiece can be captured simultaneously, thus saving time of inspecting the surfaces of the workpiece.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A light-emitting structure comprising:
two outer shells configured to join together to cooperatively define a receiving space therein;
a connecting assembly configured to join the two outer shells together; and
two light-emitting assemblies coupled to the connecting assembly and configured to emit light inside the receiving space; wherein
the two outer shells define a plurality of viewing holes therein for viewing inside the receiving space; and
the plurality of light-emitting assemblies shines light from a plurality of different angles inside the receiving space.

2. The light-emitting structure as in claim 1, wherein:
each of the two outer shells is hemispherical; and
the receiving space is spherical when the two outer shells are joined together.

3. The light-emitting structure as in claim 2, wherein each outer shell comprises:
a dome-shaped main body; and
a flange rim protruding continuously around a peripheral edge of the main body.

4. The light-emitting structure as in claim 3, wherein:
the plurality of viewing holes is defined in the main body of each outer shell;
each of the two outer shells defines a first cutout in an edge portion thereof; and
the first cutout is defined through the main body and the flange rim.

5. The light-emitting structure as in claim 4, wherein each end of the flange rim is flush with a corresponding edge of the first cutout.

6. The light-emitting structure as in claim 4, wherein the connecting assembly comprises:
a first connecting piece configured to support the plurality of light-emitting devices thereon;
a second connecting piece surrounding the first connecting piece and configured to join the two outer shells together; and
a third connecting piece surrounding the second connecting piece.

7. The light-emitting structure as in claim 6, wherein:
the first connecting piece, the second connecting piece, and the third connecting piece are circular;
the second connecting piece is located between the first connecting piece and the third connecting piece;
the radius of the first connecting piece is less than the radius of the second connecting piece, and the radius of the second connecting piece is less than the radius of the third connecting piece; and
a second cutout is defined through the first connecting piece, the second connecting piece, and the third connecting piece.

8. The light-emitting structure as in claim 7, wherein:
the first supporting piece comprises a pair of opposite supporting surfaces, each supporting surface being configured to support a corresponding light-emitting assembly thereon; and
the second supporting piece comprises a pair of opposite fixing surfaces, each fixing surface being configured to fix the flange rim of a corresponding outer shell thereon.

9. The light-emitting structure as in claim 8, wherein:
the connecting assembly defines a plurality of channels through the first connecting piece, the second connecting piece, and the third connecting piece;
an electrical connector is inserted through each channel; and
the electrical connectors are configured to electrically connect the light-emitting assemblies to a control unit to control the light-emitting assemblies to emit light.

10. The light-emitting structure as in claim 9, wherein a groove is defined between the first connecting piece and the second connecting piece on each side of the connecting assembly, the grooves being configured to receive electrical lines of the light-emitting assemblies.

11. The light-emitting structure as in claim 9, wherein:
each light-emitting assembly comprises a plurality of light-emitting devices located thereon; and
a third cutout is defined in each light-emitting assembly.

12. The light-emitting structure as in claim 11, wherein the light-emitting devices are LED lights of different colors.

13. The light-emitting structure as in claim 8, wherein:
a plurality of first fixing holes is defined in each supporting surface of the first connecting piece;
a plurality of second fixing holes is defined in each fixing surface of the second connecting piece;
a plurality of third fixing holes is defined in each light-emitting assembly, the third fixing holes corresponding to the first fixing holes;
a plurality of fourth fixing holes is defined in the flange rim of each outer shell, the fourth fixing holes corresponding to the fourth fixing holes;
each light-emitting assembly is secured to the corresponding supporting surface of the first connecting piece by a plurality of first fixing members being inserted through the first fixing holes and the third fixing holes; and
each outer shell is secured to the corresponding fixing surface of the second connecting piece by a plurality of second fixing members being inserted through the second fixing holes and the fourth fixing holes.

14. The light-emitting structure as in claim 13 further comprising:
two outer securing members, each outer securing member configured to be secured onto the flange rim of a corresponding outer shell.

15. The light-emitting structure as in claim 14, wherein:
a plurality of fifth fixing holes is defined in each outer securing member;
each outer securing member is secured to the flange rim of the corresponding outer shell by the plurality of second fixing members being inserted through the fifth fixing holes, the fourth fixing holes, and the second fixing holes; and
each outer securing member defines a fourth cutout that is aligned with the first, second, and third cutouts when the light-emitting structure is assembled.

16. The light-emitting structure as in claim 8, wherein:
each light-emitting assembly is secured to the corresponding supporting surface of the first connecting piece by an adhesive; and
each outer shell is secured to the corresponding fixing surface of the second connecting piece by an adhesive.

17. The light-emitting structure as in claim 8, wherein:
the two outer shells, the two light-emitting assemblies, and the connecting assembly share a common axis;
the two first cutouts, the second cutouts, and the two third cutouts are aligned with each other to cooperatively define an entranceway when the light-emitting structure is assembled; and
a size of the entranceway is large enough to accommodate a workpiece to pass therethrough to be received in the receiving space.

* * * * *